United States Patent
Castillo et al.

(10) Patent No.: US 10,927,231 B2
(45) Date of Patent: Feb. 23, 2021

(54) DECOMPOSITION OF CONDENSATION POLYMERS

(71) Applicant: Ioniqa Technologies B.V., Eindhoven (NL)

(72) Inventors: Sonja Irene-Marie Reginalde Castillo, Eindhoven (NL); Vincent Gertrudis Antonius Philippi, Eindhoven (NL)

(73) Assignee: Ioniqa Techonolgies B.V.

( * ) Notice: Subject to any disclaimer, the term of this patent is extended or adjusted under 35 U.S.C. 154(b) by 0 days.

(21) Appl. No.: 16/481,707

(22) PCT Filed: Jan. 30, 2018

(86) PCT No.: PCT/NL2018/050063
§ 371 (c)(1),
(2) Date: Jul. 29, 2019

(87) PCT Pub. No.: WO2018/143798
PCT Pub. Date: Aug. 9, 2018

(65) Prior Publication Data
US 2020/0024420 A1 Jan. 23, 2020

(30) Foreign Application Priority Data

Jan. 31, 2017 (NL) ...................................... 2018269

(51) Int. Cl.
*C08J 11/24* (2006.01)
*B01J 23/745* (2006.01)
(Continued)

(52) U.S. Cl.
CPC ............. *C08J 11/24* (2013.01); *B01J 23/745* (2013.01); *B01J 23/755* (2013.01); *B01J 35/026* (2013.01);
(Continued)

(58) Field of Classification Search
CPC . C08J 11/24; C08J 11/16; B01J 23/745; B01J 23/755
(Continued)

(56) References Cited

FOREIGN PATENT DOCUMENTS

JP 2012067200 A * 4/2012
JP 2012067200 A 4/2012
(Continued)

OTHER PUBLICATIONS

International Search Report and Written Opinion for International Application No. PCT/NL2018/050063, Filed Jan. 30, 2018, dated Mar. 19, 2018.

*Primary Examiner* — Deborah D Carr
(74) *Attorney, Agent, or Firm* — Husch Blackwell LLP

(57) ABSTRACT

Particles of a transition metal are used as a catalyst for depolymerisation of condensation polymers in alcohol. In the method of catalysed depolymerisation of a condensation polymer in a solid form into monomers and/or oligomers, transition metal particles; are mixed with the condensation polymer in alcohol to obtain a reaction mixture. This reaction mixture is processed to disperse the condensation polymer into the alcohol and decompose it, wherein the transition metal particles act as a catalyst and the alcohol is a reagent. The catalyst is particularly supplied as a catalyst composition of transition metal particles in an alcoholic liquid. The transition metal particles are typically non-porous and may have an oxide surface.

20 Claims, 1 Drawing Sheet

(51) Int. Cl.
    *B01J 23/755*    (2006.01)
    *B01J 35/02*     (2006.01)
    *B01J 35/10*     (2006.01)
    *B01J 37/08*     (2006.01)
    *C07C 67/60*     (2006.01)
    *C08J 11/16*     (2006.01)
(52) U.S. Cl.
    CPC ......... *B01J 35/1009* (2013.01); *B01J 37/086*
        (2013.01); *C07C 67/60* (2013.01); *C08J 11/16*
            (2013.01); *C08J 2367/02* (2013.01)
(58) Field of Classification Search
    USPC .......................................................... 560/79
    See application file for complete search history.

(56) References Cited

FOREIGN PATENT DOCUMENTS

| | | | |
|---|---|---|---|
| WO | WO 2007/076384 A2 | 7/2007 | |
| WO | WO 2014/209117 A1 | 12/2014 | |
| WO | WO-2014209117 A1 * | 12/2014 | .......... B01J 35/0033 |
| WO | WO 2016/105198 A1 | 6/2016 | |
| WO | WO-2016105198 A1 * | 6/2016 | .............. C08J 11/16 |
| WO | WO 2017/111602 A1 | 6/2017 | |

* cited by examiner

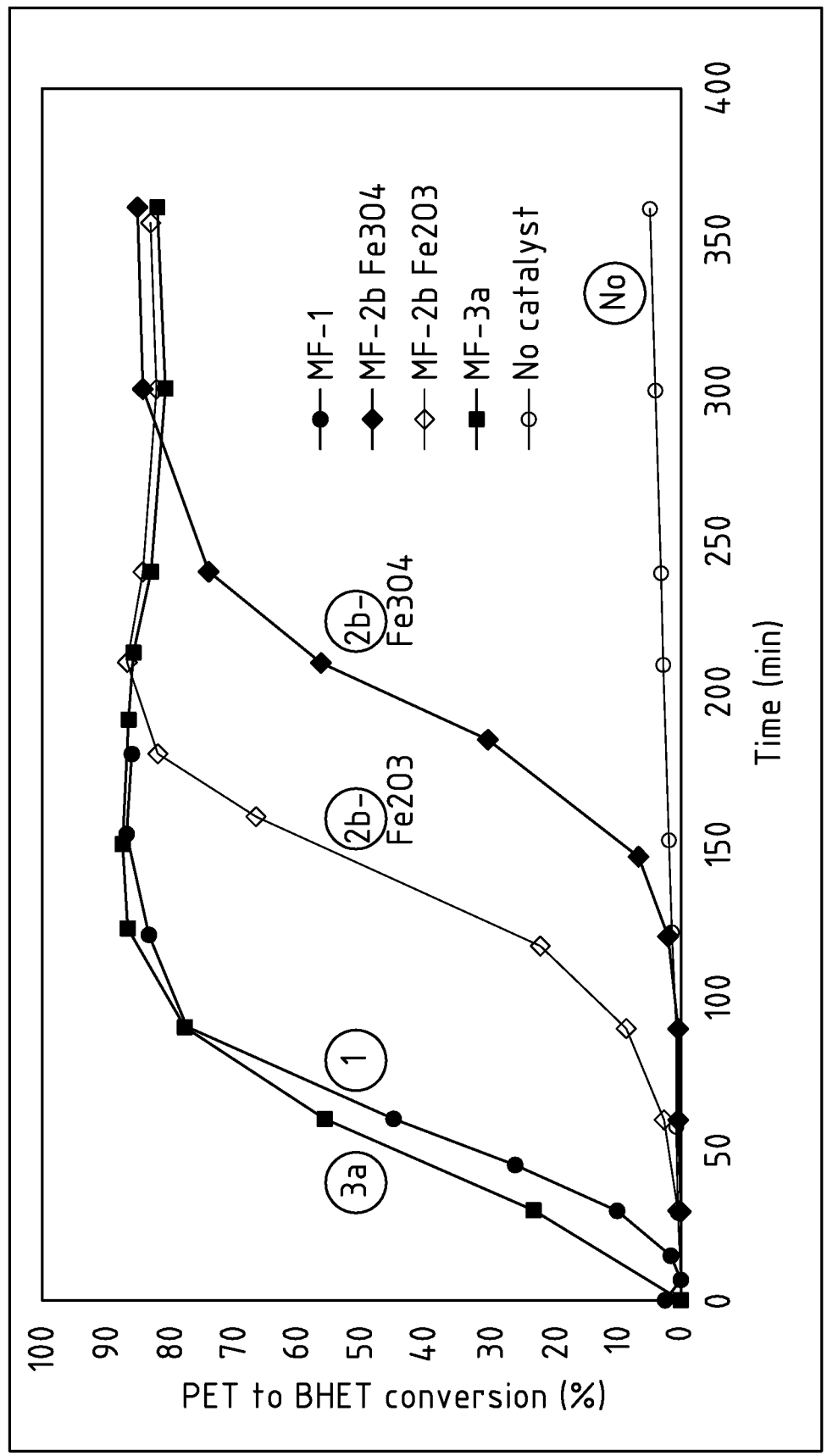

DECOMPOSITION OF CONDENSATION POLYMERS

CROSS REFERENCE TO RELATED APPLICATIONS

This is a U.S. National Stage of International Patent Application No. PCT/NL2018/050063 filed Jan. 30, 2018, which claims the benefit of and priority to Netherlands Application No. 2018269, filed Jan. 31, 2017 all of which are incorporated by reference herein in their entireties.

FIELD OF THE INVENTION

The invention relates to a method of catalysed depolymerisation of condensation polymers. The invention further relates to a catalyst composition for use in depolymerisation of condensation polymers.

BACKGROUND OF THE INVENTION

Condensation polymers such as polyesters and polyamides are produced in large quantities and used for a variety of applications, including textile materials, packaging of food and liquid cleaning compositions and industrial applications. Specifically known polyesters include polylactic acid and polyethylene terephthate (PET) and polyamides such as a variety of types of nylon, for instance nylon-6, nylon-6,6, nylon-4,6 and so on. After their use, such condensation polymers end up as waste, which needs to be processed. By lack of economic options for recovery of useful starting material, such condensation polymers are often combusted in incineration plants. One specific example hereof is PET used for textile and/or for packages such as bottles.

In order to reduce consumption of raw materials, to reduce the volume of waste and to improve sustainability in general, a significant amount of research and development has been devoted to depolymerisation processes for such polymers, and to the development of biodegradable polymers such as polylactic acids. Typically, the depolymerisation is preceded or combined with dispersion and/or dissolution of the waste polymers into a solvent or solvent mixture. Herein, the polymers are suitably separated, so as to arrive at a solution of monomers that are suitable for reuse. Reference is for instance made to WO00/29463A1.

Recently, quite some attention has been paid to nanoparticles as a depolymerisation catalyst. Such nanoparticles have a small diameter and therewith a high surface area, for instance of 10 $m^2$/g or more. This high surface area allows for significant adsorption of the condensation polymer, which is believed to result is quick depolymerisation and therewith an economically feasible process. One example is a catalyst that comprises both a nanoparticle and a functional group known per se as magnetic fluid. The latter is more particularly a positively charged organic aromatic compound. The aromatic compound suitably is a nitrogen-containing heterocyclic moiety. This may be grafted onto the nanoparticle via a bridging moiety, for instance based on an organosilicon compound. Such a catalyst is for instance disclosed in WO2016/105198A1.

However, it has been observed by the applicant that the separation of the said catalyst based on nanoparticles and the resulting solution with monomer product is not perfect. The catalyst needs to be removed from the monomer solution in order to obtain a clean monomer and to enable reuse of the nanoparticle catalyst. While the use of magnetic nanoparticles principally allows separation by means of magnetic attraction, many nanoparticles are so small that they are not attracted sufficiently. The monomer solution rather is a dispersion comprising very fine particles that are well dispersed. Such particles need to be removed by filtering and adsorption, for instance using an active carbon filter, with the result of loss of catalyst. One option to solve this problem is the generation of larger-sized clusters of nanoparticles, as described by the applicant in the non-prepublished application NL2017033.

Still, it is desirable to develop further catalysts for the depolymerisation of condensation polymers, such as polyesters and polyamides and more particularly polyethylene terephthalates and related polyesters.

SUMMARY OF THE INVENTION

It is therefore an object of the present invention to provide further depolymerisation catalysts that can efficiently be separated from the solution with monomer product, and is thus suitable for reuse.

It is another object to provide an improved depolymerisation method for condensation polymers. According to a first aspect, the invention relates to the use of particles of a transition metal as a catalyst for depolymerisation of condensation polymers in alcohol.

According to a second aspect, the invention relates to a catalyst composition comprising particles of a transition metal in an alcoholic carrier liquid, which is at least substantially water-free.

According to a third aspect, the invention relates to a method of catalytic depolymerisation of a condensation polymer into monomers and/or oligomers, which method comprises the steps of: (1) providing the condensation polymer in a solid form and further providing particles of transition metal; (2) mixing the condensation polymer with the transition metal particles in alcohol to obtain a reaction mixture; (3) processing the reaction mixture at elevated temperature, at which the condensation polymer is dispersed and optionally dissolved into the alcohol and decomposed into oligomer and/or monomer, wherein the transition metal particles act as a catalyst and wherein the alcohol is a reagent in the depolymerisation, and wherein the monomer and optionally oligomer dissolve in the alcohol to form an alcohol solution; (4) separating the alcohol solution from solids, including the transition metal particles, and (5) providing a catalyst composition comprising the transition metal particles for reuse as catalyst.

It has been observed by the inventors that transition metal particles as such turn out to be very effective as catalysts and can be effectively separated from a solution with monomer and any soluble oligomer. Preferred examples of transition metals are nickel, cobalt and iron, and more preferable nickel and iron. It is believed by the inventors, without being bound thereto, that the said iron particles catalyse the rate-limiting step in the depolymerisation, which turns out to be the release of individual molecules of the condensation polymer out of the polymeric material, which is for instance semicrystalline. This release results in dispersing of polymer material into the carrier liquid and/or dissolving of individual polymer molecules in the carrier liquid. Such dispersing and/or dissolving is believed to further involve depolymerisation from polymer into oligomers.

As a preliminary explanation, the inventors believe that a surface layer of the transition metal particle, typically oxidized, may get dissolved into the alcohol. The resulting metal ions, for instance $Fe^{2+}$ and/or $Fe^{3+}$ may be active in the catalysis. However, it may well be that not merely the dissolved metal ions contribute to catalysis, but that also the surface layer of the transition metal particle contributes, for instance in that the alcoholic carrier liquid such as a glycol would be adsorbed and be activated, enabling complexation with the carbonyl-group of the condensation polymer. Such a mechanism might explain the effective catalysis at relatively low concentration of catalyst material, which more preferably has a low surface area.

Moreover, it appears that the dissolution rate is sufficiently low so that a transition metal particle may be reused as a catalyst a plurality of times. For instance the catalyst can be reused at least five times, more preferably at least ten times, or even at least twenty times. How often a catalyst can be reused, will further depend on—among others—the concentration of catalyst, the initial size of the transition metal catalyst particle, the separation method, and the type of transition metal. However, it is quite surprising for the inventors that the transition metal particles that are apparently able to be dissolved, anyhow survive a single run, in which the temperature exceeds 150° C. and preferably is in the range of 180-220° C., further dependent on the used alcohol. One explanation is the transition metal would not dissolve into the alcohol, except upon interaction with the alcohol and/or with carbonyl (C=O) groups in the condensation polymer. Another explanation is that the alcohol adsorbs on the surface of the particle and possibly by forming an alkoxide bond (TM-O-C, wherein TM refers to a transition metal). This adsorption may limit dissolution, and may at the same time resulting in activation towards the condensation polymer, and particularly any carbonyl group therein.

In a preferred embodiment, the transition metal is chosen from the first series of transition metals, also known as the 3d orbital transition metals. More particularly, the transition metal is chosen from iron, nickel and cobalt. Since cobalt however is not healthy and iron and nickel particles may be formed in pure form, iron and nickel particles are most preferred. Furthermore, use can be made of alloys. Most preferred is the use of iron particles. Iron particles have been found to catalyse the depolymerisation of PET to conversion rates into monomer of 70-90% within an acceptable reaction time of at most 6 hours. The needed concentration of catalyst is 1 wt % relative to the amount of PET or less. Good results also have been achieved with a catalyst loading below 0.2 wt % and even below 0.1 wt %. Such a low loading of the catalyst is highly surprising and also beneficial, since a low catalyst loading results in a lower dissolution of catalyst into the alcohol and therewith less ions to be removed again, for instance by means of an absorption treatment, suitably with an active carbon column.

In one suitable embodiment, use is made of transition metal particles in the range of 0.5-50 μm. The size range herein defines the diameter. The diameter is herein measured by means of electron microscopy. Particles in this size range are sufficiently big to be separated from the product solution by means of a conventional separation technology such as filtering or a centrifuge treatment. At the same time, they are sufficiently small to obtain a good distribution of the particles and to allow that the particle surface may get close to the solid polymer, resulting in highly effective catalysis. A preferred particle size is from 1-10 μm.

Advantageously, the transition metal particles, such as nickel particles and iron particles, have a low surface area and are substantially non-porous. Suitably, the surface area is less than 3 $m^2/g$, preferably at most 1 $m^2/g$ or even less than 0.6 $m^2/g$. The porosity is suitably less than $10^{-2}$ $cm^3/g$ or even less for instance at most $10^{-3}$ $cm^3/g$. It has been found that such non-porous transition metal particles can be suitably prepared by thermal decomposition of carbonyl complexes such as iron pentacarbonyl and nickel tetracarbonyl. The inventors have understood that a non-porous particle tends to be more suitable than a porous particle, since its exposure to the alcohol is less, and therefore, the corrosion of the particle is less and the particle can be reused more often for catalysis. Furthermore, due to the limited surface area, any oxidation at the surface results in a low quantity of metal-ions and therewith a low level of ions that are present in the product stream as a contaminant to be removed therefrom.

In again one further embodiment, the transition metal particle is an iron particle, and it is further provided with an iron oxide surface. The presence of an iron oxide surface may further enhance catalysis. The oxide surface may be formed by itself, in contact with air, in contact with water, or the oxide surface may be applied deliberately.

The alcohol is preferably chosen from the group of aliphatic alcohols. Suitably, use is made of an alcohol with a boiling point above 150° C. which is further able to participate in the decomposition of the condensation polymer as a reagent. In this perspective, polyols are preferred. Suitable polyols are for instance glycerol, propylene glycol and ethylene glycol. A most preferred alcohol is ethylene glycol. This results in glycolysis of the condensation polymer, more particularly the ester. Due to the presence of two alcohol-groups per molecule, the monomer is provided with one free alcohol-group, and is therewith capable of reacting again with an acid to form an ester. Such free alcohol-group would not be available, when use is made of monoalcohols, such as methanol. It is not excluded to use a mixture of alcohols. A mixture of an alcohol and another polar organic solvent, such as a keton or aldehyde are not excluded. However, it is preferred that merely one alcohol would participate as a reagent in the decomposition, so as to prevent formation of different monomers.

The condensation polymer is generally chosen from the group of polyesters, polyamides, polyimides and polyurethanes. In an example the polymer is at least one of a polyester, a polyether, such as poly-oxymethylene (POM), polyethylene glycol (PEG), polypropylene glycol (PPG), polytetramethyleneglycol (PTMG), polyethylene oxide (PEO), polypropylene oxide (PPO), polytetrahydrofuran (PTHF), and polytetramethyleneetherglycol (PTMEG), a polypeptide, a polyamide, such as any type of nylon, including nylon-6 and nylon-6,6, a polyamine, a polycondensate, preferably a polyester, such as poly carboxylic ester, wherein the poly carboxylic ester is preferably selected from polyethylene terephthalate (PET), polyethylene furanoate (PEF), polybutylene terephthalate (PBT), polytrimethylene terephthalate (PTT), polyglycolic acid (PGA), polylactic acid (PLA), polycaprolactone (PCL), polyethylene adipate (PEA), polyhydroxyalkanoate (PHA), polyhydroxybutyrate (PHB), polyethylene naphthalate (PEN), Poly(3-hydroxybutyrate-co-3-hydroxyvalerate) (PHBV), and a polycondensate of 4-hydroxybenzoic acid and 6-hydroxynaphthalene-2-carboxylic acid (VECTRAN). Representative examples include PET (polyethylene terephthalate). PEF (polyethylene furanoate), PTT (polytrimethylene terephthalate), PLA (polylactic acid). Most preferred are PET, PTT and PEF. The condensation polymer is more preferably a waste polymer, i.e. a polymer in the form of an article such as a bottle or as part of textile that has been recycled and is then optionally processed into an appropriate shape for depolymerisation. An example of such optional (pre-)processing is the subdivision of the articles into smaller parts, for instance parts with a typical size of 2×2 cm or less, and typically at least 0.2×0.2 cm. Another example of such preprocessing is any separation of polymers in the waste polymer product, such as a separation between nylon and PET. Again another example of such optional preprocessing is a preheating step in the alcohol.

A preferred process for the depolymerisation of the condensation polymer, such as PET, is specified in the method of catalytic depolymerisation as specified hereinabove and including several steps. Such process involves after the provision of the catalyst, the condensation polymer and the alcohol the heating to elevated temperature, so as to achieve an acceptable reaction rate; the dispersing of the solid condensation polymer into the alcohol (said dispersing typically also comprising at least some depolymerisation), the decomposition of the condensation polymer into oligomers and monomers, and the separation of a solution with the dissolved monomers and any dissolved oligomers on the one hand and non-dissolved parts on the other hand. The non-dissolved parts typically comprise the transition metal particles, thus the catalyst. Further non-dissolved parts may include any pigment, dyes or other colorants and fillers present in the solid condensation polymer, any oligomer to the extent that is not fully dissolved, and any polymers of a different type that have not been depolymerised.

The elevated temperature is for instance a temperature that is at most 20° C. lower than the boiling point of the alcohol used. In the case of depolymerisation of polyesters such as PET, ethylene glycol is the preferred alcohol, and the elevated temperature is suitably in the range of 180-200° C. The dispersing of the solid condensation polymer and the decomposition of the condensation polymer into oligomers and monomers may occur simultaneously. It is believed that the present catalyst particularly accelerates the first step of dispersing, possibly combined with some depolymerisation. In view thereof, it is believed that the present catalyst composition is particularly suitable for the degradation of a semicrystalline polymer.

Preferably, said method includes one or more steps wherein catalyst is removed from the product. Typically, removal of the catalyst composition from a product stream involves a solid-liquid separation. Dependent on the particle size and material, a preferred solid-liquid separation technology may be chosen. The catalyst composition of the present invention comprising micron-sized magnetic particles may for instance be separated from the liquid by means of magnetic separation, centrifugation, filtration or membrane filtration. In one preferred embodiment, use is made of centrifugation, which is an industrially viable technology. In another preferred embodiment, use is made of filtration, more preferably microfiltration, which is one form of membrane filtration, or alternatively by means of a conventional filter with pore size of 1 micron. These are cost effective separation techniques for micron-sized particles. Preferably, the filtration step is carried out at temperatures above 80° C. This is deemed suitable to ensure an adequate processing and prevent viscous behaviour of the reaction mixture. Most preferably, use is made of a hydrophobic polymer membrane, such as based on polypropylene (PP), polyethylene (PE) and/or polytetrafluoroethylene (PTFE). Such membrane filters are not sensitive for degradation by means of the catalyst composition, whereas ester-based filters typically are and may cause contamination of the product stream. A membrane filter of a PTFE membrane is deemed suitable, as it may be operated at temperatures well above 80° C., for instance in the range of 120-180° C. The filter size can be chosen in the range of 0.1-4 microns, such as 0.5-1 micron, further dependent on the particle size of the resulting product.

In the context of the depolymerisation process according to the invention, it is furthermore deemed suitable to separate monomer from oligomer and/or any polymer. Most suitably, use is made of water, which results in solidification of oligomers, while monomers remain dissolved in the aqueous alcoholic mixture. This was found to be an efficient method of obtaining a substantially pure product.

In a preferred embodiment, the process is configured so as to remove the transition metal particles from the reaction mixture prior to adding water. This is deemed preferable, so as to prevent oxidation of the transition metal particles by means of the water, which will increase the concentration of ions in the resulting product stream comprising monomers. As discussed above, the catalyst is for instance removed by means of filtration or membrane filtration.

In again a further embodiment, a further additive is added to the reaction mixture at any suitable stage in the process. This further additive is added to ensure that at least selected colorants are removed from the product stream. More particularly, the additive is of a particulate nature and comprises particles to which are grafted functional groups comprising a bridging moiety and a colour adsorbing entity. The bridging moiety comprises a functional group for adhesion or bonding to the particulate body and a linking group towards the colour adsorbing entity, and wherein the colour adsorbing entity comprises a positively charged moiety comprising a heteroatom, preferably a heterocyclic aromatic moiety. The particles may be nanoparticles or larger particles or aggregates of nanoparticles, such as described in the non-prepublished application NL2017033, which is herein included by reference. Said additive is understood to ensure that colour is included in a solid mixture of colorant, oligomer and/or any polymer, which solid mixture is formed, in one suitable embodiment, upon the addition of water. It is observed that the additive described in said non-prepublished application is also known as a catalyst for depolymerisation. However, when added as an additive for colour removal, it may be present in smaller quantities, for instance in amounts of less than 1 wt %, or preferably less than 0.5 wt %, or even less than 0.2 wt %. Also, the particles may have larger dimensions. Furthermore, if so desired, said additive may be added at a later stage of the process, for instance after removal of the transition metal particles.

The invention further relates to a catalyst composition. Herein, the transition metal particles are dispersed into a carrier liquid which composition is substantially free of water. Preferably, the carrier liquid comprises at least one alcohol. More preferably, the alcohol is suitable as a solvent and reagent during the depolymerisation of the condensation polymer. A very suitable example of an alcohol is a glycol, such as ethylene glycol. It is the insight of the inventors that by means of the dispersion of the transition metal particles, more particularly iron particles or nickel particles, and more particularly micron-sized iron particles obtainable by thermal decomposition of iron-pentacarbonyl, oxidation of the iron particles is inhibited or entirely stopped. Therewith, the properties of the catalyst particles are maintained for a sufficient period to enable storage and transport. This is deemed particularly relevant, to reduce dissolution of iron ions into the solvent(s) of depolymerisation. It is observed that dissolved iron ions need to be removed again from the product stream comprising the monomer, such as the monomer of PET, since the specifications for metal ions in the said product stream are very strict. Suitably, the content of transition metal particles in the catalyst composition is in the range of 5-20 wt %, such as 7-15 wt %.

In a further embodiment, the catalyst composition further comprises further particles to which are grafted catalytic groups comprising a positively charged organic compound (or group). More particularly, the charged organic compound is a heterocyclic and particularly heteroaromatic compound, such as a compound containing a pyridinium, an imidazolium, a piperidinium, a pyrrolidinium, a pyrazolium, a thiazolium, a quaternary ammonium or a quaternary phosphonium ion, wherein said ions are substituted with one or more alkyl-groups. One of said alkyl groups, typically, C2-C6 alkyl, is provided with a linking group for adsorption and/or reaction to the surface of the particles. Suitable linking groups are carboxylic acid groups and silanol groups as typically derived from tetraethylene-orthosilicate (TEOS). Most preferably, the positively charged organic compound contains an imidazolium-ion, for instance a dialkyl-imidazolium-ion, such as an alkyl-imidazolium-$C_2$-$C_4$-alkyl-trialkoxysilane, which will react with the particle surface as a silanol-group derived from one or more of said trialkoxy-groups. The particles may herein be the micron-sized transition metal particles, but is alternatively and preferably distinct particles. The size of the particles is for instance from 2 nm to 10 microns. Suitably, use is made of particles in the range of 100 nm to 10 microns, more preferably from 200 nm to 5 microns or even from 400 nm to 2 microns. The size is herein defined as defined by electron microscopy. It refers to a size range such that at least 90 vol % of the particles has a size within the said range, more preferably at least 95 vol % or even at least 98 vol % of the particles. The nature of the particles used herein may be variable, for instance an iron oxide or other oxide, more particularly a ferrite such as hematite, magnetite, maghemite. One example hereof is known from WO2016/105198A1. More preferably, use is made of the clustered catalyst particle described in the non-prepublished application NL2017033, which is herein included by reference. In order to achieve removal of colourants without the risk that such particles end up in the aqueous product stream, particles with a larger particle size such as at least 100 nm are deemed preferred. The particles suitably have a surface area of at least 5 $m^2/g$, preferably a surface area of at least 10 $m^2/g$. It has been found that particles containing such a charged organic compound are suitable per se as a catalyst for depolymerisation, but also result in removal of colourants from a typically aqueous product stream comprising monomer. As to the mechanism of colour removal, it is believed by the inventors that the colourant molecules are attracted to the positively charged organic group. Upon addition of water, the particles may act as substrates onto which solidification of the oligomers and/or any polymers occurs. The colour is then trapped into the solid phase. It is observed that the said particles with color removal groups attached thereto may further contribute to the degradation of the polymer.

In again a further embodiment, the catalyst composition comprises a ionic liquid. Such a ionic liquid suitable contains a charged organic compound of the type identified hereinabove and any counterion. The addition of a ionic liquid to the composition, wherein it is dissolved into the alcoholic carrier liquid is understood to contribute to colour removal.

In one further embodiment, the catalyst composition further comprises a dispersing agent. Such a dispersing agent is suitable to prevent any adhesion of the particles to each other. Preferably, use is made of a dispersing agent that is not charged and does not use counter-ions, so as to keep the concentration of ions as low as possible. The use of dispersing agents with one or more anchoring sites for adsorption to the particle surface and one or more stabilizing groups extending into the carrier liquid is deemed preferred. Suitable stabilizing groups include for instance oligo(alkyleneoxides), wherein alkylene is ethylene, propylene and/or butylenes. Suitable groups for anchoring include carboxylic acids groups, silanol-groups, for instance derived from TEOS.

BRIEF INTRODUCTION OF THE FIGURES

These and other aspects will be further elucidated with reference to the FIGURE and the examples, in which:

FIG. 1 shows a graph of the conversion of polyethylene terephthalate (PET) in solid form to monomer (BHET) as a function of time for different catalysts.

EXAMPLES

Example 1

Several catalysts 1, 2b-1, 2b-2 and 3a were prepared. Catalyst 1 was the catalyst as described in non-pre-published application NL2017033, which is included herein by reference. The catalyst comprises 100-200 nm aggregates of magnetite nanoparticles of 10 nm diameter, onto which were grafted a combination of a 3-[butyl-imidazolium]-propyl-triethoxysilane. In the grafting process, one or more of the ethoxy-groups were removed to obtain a silanol-bond. Catalysts 2b-1 and 2b-2 were commercially available iron oxide ($Fe_2O_3$ and $Fe_3O_4$, respectively) with a diameter in the order of 0.5 µm. Catalyst 3a was obtained through thermal decomposition of iron-pentacarbonyl ($Fe(CO)_5$ distilled previously to high purity, and was commercially obtained from Sigma-Aldrich. Properties of catalyst 3a and various modifications thereof are known from K. Sugimura et al, *AIP Advances* 6(2016), 055932. The catalyst 3a was provided with an iron oxide surface. Furthermore an experiment was carried out without catalyst.

All catalysts were used in a ratio of 1 wt % catalyst relative to the polyethylene terephthalate (PET). The PET was provided was PET flakes with an average size of about 1×0.5 cm. The PET flakes were prepared from transparent PET bottles. The PET flakes were weighted to obtain a 12 wt % dispersion in ethylene glycol. Catalyst compositions were prepared by dispersing the catalyst into ethylene glycol so as to provide dispersions of 10 wt %. The catalyst dispersion was homogenised by shaking vigorously for 5 minutes by hand. Thereafter, further ethylene glycol was added to dilute the catalyst composition to the desired density. Then, the PET flakes were added and the round bottom flask was placed in the heating set up. The heating was started and within 20 minutes, the reaction mixture had reached the reaction temperature of 190-200° C. The reaction was followed in time by taking in-process-control samples to measure the concentration of the monomer produced as a function of time. This monomer is Bis-(2-hydroxyethyl) terephthalate, also referred to as BHET. The concentration of BHET was determined with HPLC. The results are shown in FIG. 1. It was found that the depolymerisation with catalyst 1 and catalyst 3a occurred at a rate that was almost identical. After approximately 2 hours, a conversion to BHET of 80-85% was reached. Thereafter, no further increase in BHET was obtained. Such a conversion of 80-90% is deemed to be a maximum equilibrium conversion. Conversely, the iron oxide catalysts 2b-1 and 2b-2 reached a conversion of more than 80% only after 5 hours and 3.5 hours respectively. Without catalyst, a conversion of 5% was achieved in 6 hours.

Example 2

Surface area of the catalysts was characterized by means of adsorption experiments using the BET-method as known per se in the art. Use was made of services of the Technical University of Delft and Delft Solids Solutions, using a Micromertics Tristar 3000 apparatus. Results are shown in Table 1.

TABLE 1 surface area of catalysts

| Catalyst | Size | Surface area (m$^2$/g) |
| --- | --- | --- |
| 1 | ≤200 nm | ≥20 |
| 2b-1 | ~500 nm | 5 |
| 2b-2 | ~500 nm | 10 |
| 3a | 1-5 μm | 0.4-0.5 |

It is apparent that the catalyst 3a has a very small surface area (about 50 times less than catalyst 1), which however does not reduce the depolymerisation rate.

Example 3

Catalyst 3a was used in a ratio of 1 wt % relative to the PET, in the manner as identified in Example 1, and on labscale. After the predefined depolymerisation time, the reaction mixture was cooled down by adding water. This further resulted in solidification of oligomers. The solids were thereafter separated from the liquid by means of a magnet. I.e. A magnet was applied at an outside of a reaction vessel in the form of a glass beaker. The iron particles were thereafter reused as a catalyst without any further processing or purification. It was found that the iron particles could be reused at least 20 times without loss of catalytic activity.

The invention claimed is:

1. A method of depolymerisation of condensation polymers in alcohol, wherein use is made of particles of a transition metal as a catalyst for said depolymerisation of condensation polymers, wherein the transition metal particles are at least substantially non-porous.

2. The method as claimed in claim 1, wherein use is made of transition metal particles in the range of 0.5-50 μm.

3. A method of depolymerisation of condensation polymers in alcohol, wherein use is made of particles of a transition metal as a catalyst for said depolymerisation of condensation polymers, wherein the transition metal particles have a surface area of less than 3 m$^2$/g.

4. The method as claimed in claim 1, wherein use is made of iron, nickel or cobalt particles.

5. The method as claimed in claim 4, wherein the iron particles are obtained by thermal decomposition of iron pentacarbonyl, the nickel particles are obtained by thermal decomposition of nickel tetracarbonyl, and the cobalt particles are obtained by thermal decomposition of cobalt tetracarbonyl.

6. The method as claimed in claim 4, wherein the iron, nickel or cobalt particles have an iron oxide surface.

7. The method as claimed in claim 1, wherein the condensation polymer is a waste polymer.

8. The method as claimed in claim 1, wherein the condensation polymer is chosen from the group of polyesters, polyamides, polyimides and polyurethanes.

9. The method as claimed in claim 8, wherein the condensation polymer is polyethylene terephthalate.

10. Catalyst composition comprising transition metal particles with a size in the range of 0.5-50 μm in an alcoholic carrier liquid, which composition is substantially free of water, wherein the iron particles are obtained by thermal decomposition of iron pentacarbonyl, and the nickel particles are obtained by thermal decomposition of nickel tetracarbonyl.

11. Catalyst composition as claimed in claim 10, wherein the transition metal particles are chosen from nickel particles and iron particles.

12. Catalyst composition as claimed in claim 11, wherein the particles are iron particles and are provided with an iron oxide surface.

13. Catalyst composition as claimed in claim 10, wherein the transition metal particles have a surface area of less than 3 m$^2$/g.

14. Catalyst composition as claimed in claim 10, wherein the carrier liquid comprises a polyol.

15. Catalyst composition as claimed in claim 10, further comprising further particles to which are grafted functional groups comprising a bridging moiety and a colour adsorbing entity, wherein the bridging moiety comprises a functional group for adhesion or bonding to the particulate body and a linking group towards the colour adsorbing entity, and wherein the colour adsorbing entity comprises a positively charged moiety comprising a heteroatom.

16. Catalyst composition as claimed in claim 10, further comprising a dispersing agent.

17. The method as claimed in claim 1 comprising the steps of:
Providing the condensation polymer in a solid form and further providing the transition metal particles;
mixing the condensation polymer with the transition metal particles in alcohol to obtain a reaction mixture;
processing the reaction mixture at elevated temperature, at which the condensation polymer is dispersed into the alcohol and decomposed into oligomer and/or monomer, wherein the transition metal particles act as a catalyst and the alcohol is a reagent, and the monomer and optionally oligomer is dissolved in the alcohol to form an alcohol solution;
separating the alcohol solution from solids, including the transition metal particles,
providing a catalyst composition comprising the transition metal particles for reuse as catalyst,
wherein the alcohol comprises one or more aliphatic alcohols and the elevated temperature is chosen as a temperature in the range of 20 to 0 degrees below a boiling point of the one or more alcohols.

18. The method as claimed in claim 3, wherein use is made of iron, nickel or cobalt particles.

19. The method as claimed in claim 18, wherein the iron particles are obtained by thermal decomposition of iron pentacarbonyl, the nickel particles are obtained by thermal decomposition of nickel tetracarbonyl, and the cobalt particles are obtained by thermal decomposition of cobalt tetracarbonyl.

20. The method as claimed in claim 18, wherein the iron, nickel or cobalt particles have an iron oxide surface.

* * * * *